(12) United States Patent
Errington et al.

(10) Patent No.: US 6,350,587 B1
(45) Date of Patent: Feb. 26, 2002

(54) BACILLUS STRAIN AND ANTIBIOTIC SCREENING METHOD

(75) Inventors: Jeffery Errington; Ling Juan Wu, both of Oxford (GB)

(73) Assignee: ISIS Innovation Limited, Oxford (GB)

( * ) Notice: Subject to any disclaimer, the term of this patent is extended or adjusted under 35 U.S.C. 154(b) by 0 days.

(21) Appl. No.: 09/319,777

(22) PCT Filed: Dec. 10, 1997

(86) PCT No.: PCT/GB97/03401

§ 371 Date: Jun. 11, 1999

§ 102(e) Date: Jun. 11, 1999

(87) PCT Pub. No.: WO98/26087

PCT Pub. Date: Jun. 18, 1998

(30) Foreign Application Priority Data

Dec. 12, 1996 (GB) ............................................. 9625825

(51) Int. Cl.$^7$ .............................. C12Q 1/18; C12Q 1/02
(52) U.S. Cl. ................................ 435/32; 435/6; 435/41; 435/69.8; 435/243; 435/252.3; 435/252.31; 435/440; 435/29
(58) Field of Search ................................ 435/32, 6, 41, 435/69.8, 243, 252.3, 252.31, 440, 29

(56) References Cited

FOREIGN PATENT DOCUMENTS

WO        97 00325 A      1/1997

OTHER PUBLICATIONS

S. R. Patridge et al., "The importance of morphological events and intercellular interactions in the regulation of prespore-specific gene expression during sporulation in *Bacillus subtilis*", Molecular Microbiology, vol. 8, No. 5, pp. 945–955, 1993.

D. Sun et al., "Effect of chromosome location of *Bacillus subtilis* forespore genes on their spo gene dependence and transcription by Eo$^F$: Identification of features of good Eo$^F$–dependent promoters", Journal of Bacteriology, vol. 173, No. 24, pp. 7867–7874, Dec. 1991.

K. Ireton et al., "*spoOJ* is required for normal chromosome segregation as well as the initiation of sporulation in *Bacillus subtilis*", Journal of Bacteriology, vol. 176, No. 17, pp. 5320–5329, Sep. 1994.

M. Sharpe et al., "The *Bacillus subtilis soj–spoOJ* locus is required for a centromere–like function involved in prespore chromosome partitioning", Molecular Microbiology, vol. 21, No. 3, pp. 501–509, 1996.

Sharpe et al. Postseptational chromosome partitioning in bacteria, Proc. Natl. Acad. Sci. USA 92: 8630–8634, Sep. 1995.*

* cited by examiner

*Primary Examiner*—Rebecca E. Prouty
*Assistant Examiner*—Richard Hutson
(74) *Attorney, Agent, or Firm*—Wenderoth, Lind & Ponack, L.L.P.

(57) ABSTRACT

A Bacillus strain has a chromosome with the following modifications: a mutation of a spoIIIE gene which blocks transfer of the prespore chromosome; a mutation which prevents loss of SpoOJ function from blocking sporulation; a first reporter gene dependent on $\sigma^F$ factor and placed at a location where impaired SpoOJ function leads to increased trapping in the prespore; and a second reporter gene having a promoter which is dependent on $\sigma^F$ factor and where impaired SpoOJ function leads to reduced trapping in the prespore. The strain is useful in a method of screening for putative antibiotics.

7 Claims, 1 Drawing Sheet

BACILLUS STRAIN AND ANTIBIOTIC SCREENING METHOD

BACKGROUND OF THE INVENTION

1. Field of the Invention

The present invention is related to a mutant Bacillus strain and a antibotic screening method using the same.

2. Description of the Related Art

We previously showed that the SpoIIIE protein of *Bacillus subtilis* is required for the transfer of the prespore chromosome through the asymmetric division septum that separates the prespore from its larger mother cell (1,2). spoIIIE mutations lead to a block in sporulation, leaving the prespore with only part of a chromosome, the remainder of the chromosome being trapped in the mother cell compartment. Further analysis of spoIIIE mutants has revealed that the small segment of DNA that is trapped in the prespore is a fairly specific one, centred close to the origin of DNA replication, oriC (1,3). This implied the existence of a mechanism which imposes a specific orientation on the chromosome destined for the prespore before septation. We have recently shown that the spoOJ gene is required to specify this orientation (4). However, specificity is not completely lost in spoOJ mutants (3), so it appears that there must be at least one secondary mechanism working to determine chromosome orientation at the onset of sporulation. The assay for inhibitors of SpoOJ function described below exploits some unexpected features of this change of specificity.

The spoOJ gene is highly conserved in a wide range of bacteria (5) and it is related to a family of proteins required for accurate partitioning of low-copy-number plasmids found in many diverse bacteria (6,7). Our recent results strongly suggest that SpoOJ protein has a direct role in segregation of sister chromosomes during both growth and sporulation (10). However, the gene is not essential for vegetative growth, although chromosome partitioning is partially impaired (8). Most likely, this is because of the presence of a secondary partitioning system in this organism, perhaps the same one that we have detected in the experiments mentioned above. Nevertheless, there is at least one report of a chromosomal spoOJ-like gene being essential (9), consistent with the vital importance of chromosome partitioning mechanisms for bacterial viability. Thus, the spoOJ family of proteins may be good targets for antimicrobial agents.

SUMMARY OF THE INVENTION

The effects of spoOJ mutations on prespore chromosome orientation, and the ability to detect this by use of a spoIIIE mutant background, provides the potential for a very specific whole-cell assay for inhibitors of SpoOJ function. The presence of any given segment of chromosomal DNA in the prespore can be detected by use of a reporter gene controlled by a transcription factor, $\sigma^F$, which is activated only in the is small prespore compartment (a process that is not affected by perturbations in chromosome partitioning).

Thus the invention provides in one aspect a Bacillus strain having a chromosome with the following modifications:

a) a mutation of a spoIIIE gene which blocks transfer of the prespore chromosome, b) a mutation which prevents loss of SpoOJ function from blocking sporulation, together with c) a first reporter gene having a promoter which is dependent on $\sigma^F$ factor and placed at a location where impaired SpoOJ function leads to increased trapping and hence to increased expression in the prespore, and/or d) a second reporter gene having a promoter which is dependent on $\sigma^F$ factor and placed at a location where impaired SpoOJ function leads to reduced trapping and hence to reduced expression in the prespore.

In another aspect, the present invention provides a method of determining whether an agent inhibits SpoOJ function in Bacillus species, which method comprises inducing the Bacillus strain as described to divide asymmetrically, as during sporulation, in the presence of the agent, and observing expression of the first and/or the second reporter gene.

In another aspect, the present invention provides a method which comprises inducing the Bacillus strain as described to sporulate in the presence of an agent, observing expression of the first and/or second reporter gene and thereby determining that the agent inhibits SpoOJ function in the Bacillus species, and using the agent as an antibiotic to kill or inhibit the growth of bacteria.

DESCRIPTION OF THE PREFERRED EMBODIMENTS

Figure 1:
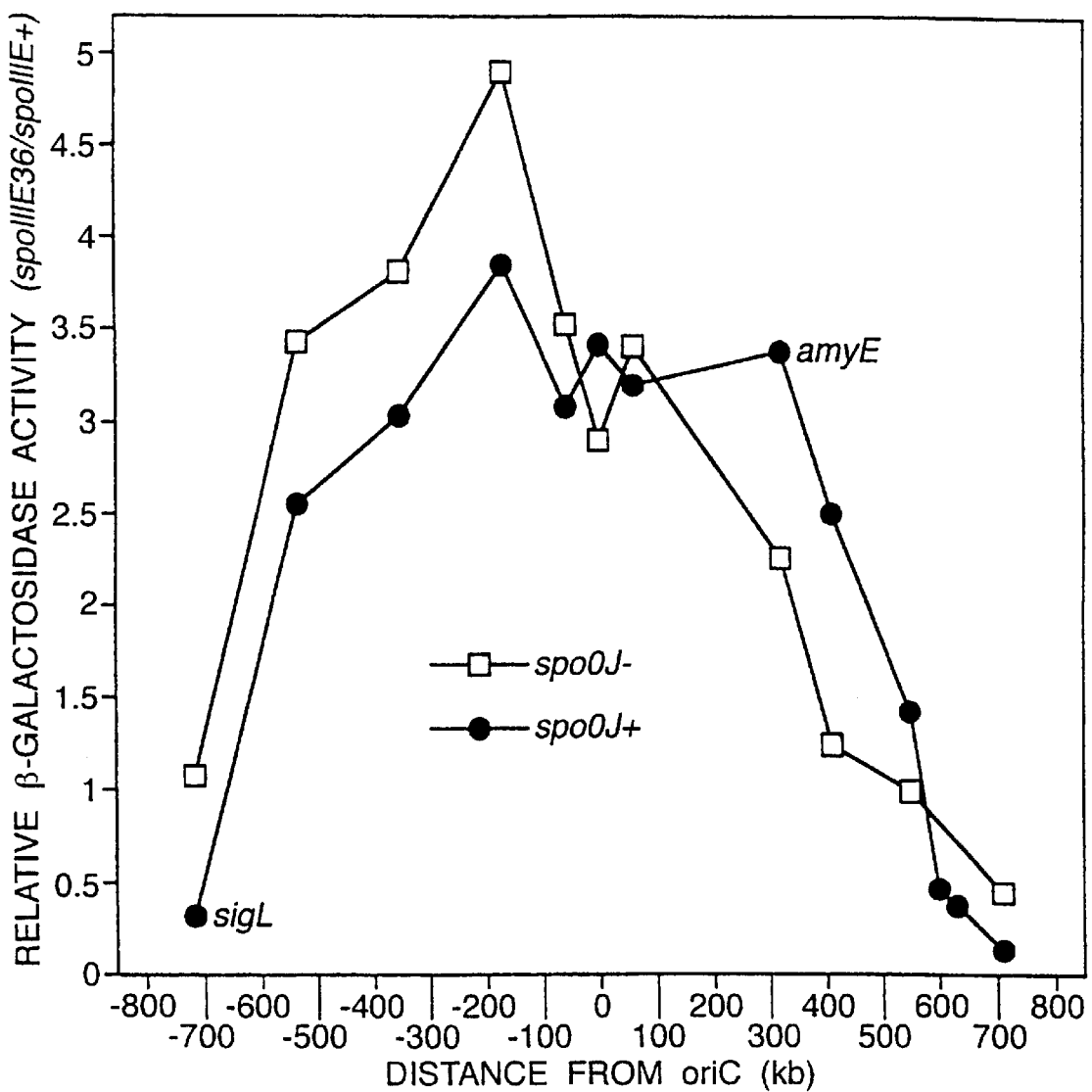
FIG. 1 shows the effect of a SpoOJ mutation on expression of $\sigma^F$-dependent reporter gene placed at different chromosomal locations in a spoIIIE background.

Preferably both the first reporter gene c) and the second reporter gene d) are present in the Bacillus strain of the invention. Preferably each of the first reporter gene c) and the second reporter gene d) is fused to a $\sigma^F$ dependent gpr promoter. Preferably each of the first reporter gene c) and the second reporter gene d) expresses a different detectable enzyme.

In the method of the present invention, expression of the first and second reporter genes is preferably observed by monitoring changes in the levels of or the ratio of their products. Preferably, the first and second reporter genes are expressed as enzymes whose activities are observed by any convenient means e.g. fluorimetry or spectrophotometry. Preferably, the Bacillus strain is induced to sporulate and is contacted, just prior to asymmetric cell division, with the agent being investigated. The method can conveniently be performed as a screening test for putative antimicrobial agents.

Any Bacillus species may be used that is capable of sporulating under suitable conditions and for which genetic constructions can be made. *B subtilis* is conveniently accessible and well characterised and thus is preferred.

Experiments with reporter genes placed at many locations in the chromosome have shown that in a spoIIIE mutant a fairly specific segment of DNA is trapped in the prespore compartment (1, 3). Loss of the spoOJ gene results in a change in the specificity of the segment of DNA that is trapped, which leads to characteristic changes in the levels of expression of $\sigma^F$-dependent reporter genes placed at different chromosomal locations. FIG. 1 shows the effect of a spoOJ mutation on expression of a $\sigma^F$-dependent reporter gene (gpr-lacZ) placed at different chromosomal locations in a spoIIIE36 background. To control for day to day variation in absolute β-galactosidase levels, each experiment was done with a control strain comprising the reporter at the same location in a spoIIIE+background. Each activity is expressed relative to that of the corresponding control. Thus, for example when a spoOJ mutation is combined with the spoIIIE mutation, expression of the reporter gene increases at the sigL location but decreases at the amyE location. Loss of SpoOJ function can therefore be detected by the large change that characteristically occurs in the levels of the products of the two reporters.

A preferred assay strain (e.g. 1238) contains several genetic modifications. First, a point mutation in the spoIIIE gene to block transfer of the prespore chromosome. The spoIIIE36 mutation is a convenient, well characterised, example of the appropriate type (1, 2). Second, a soj mutation, to prevent the loss of SpoOJ function from blocking sporulation (8). Any mutation abolishing soj function without unduly affecting expression of the adjacent spoOJ gene; such as the large in-frame deletion constructed by Ireton et al (8) would be appropriate. Third, a reporter gene, lacZ, fused to the $\sigma^F$-dependent gpr promoter and placed at the sigL location, where impaired SpoOJ function leads to increased trapping in the prespore and thus increased synthesis of the reporter gene product, β-galactosidase. Fourth, a second reporter gene, similar to the first but placed at the amyE location, where trapping and thus expression is reduced when SpoOJ function is impaired, and based on the gus gene (also called uidA), encoding, β-glucuronidase. In the absence of inhibitors of SpoOJ, sporulating cells of this strain produce considerably more β-glucuronidase than β-galactosidase. Inhibitors of SpoOJ would result in a dramatic change in the ratio, with decreased β-glucuronidase and increased β-galactosidase. Non-specific inhibitors affecting cell viability, ability to sporulate, activation of $\sigma^F$, or one or other of the reporter enzymes, would not produce this characteristic change.

The assay could be readily adapted to run on a high throughput basis, so as to enable the screening of large libraries of compounds. Strain 1238 would be grown in large batch culture in a hydrolysed casein growth medium and induced to sporulate by harvesting and resuspension in a starvation medium, according to standard practice (11, 12). Samples of the sporulating culture would then be dispensed into the individual wells of microtitre plates containing potential inhibitors. After an appropriate period of incubation, to allow activation of $\sigma^F$ and expression of the two reporter genes, the cells would be lysed and assayed simultaneously for the two enzyme products. In the case of β-galactosidase and β-glucuronidase, there are a range of substrates available for assaying the specific enzyme activities. These can give fluorescent, chemiluminescent or coloured products, which could be measured either on a continuous or a fixed time basis, using automated plate readers. Potential inhibitors could be reinvestigated in more detail using other assay methods or bacterial strains with different combinations of reporter genes. They should also produce characteristic changes in the microscopic appearance of sporulating cells (4).

REFERENCES

1. Wu, L. J. and Errington, J. (1994). *Bacillus subtilis* SpoIIIE protein required for DNA segregation during asymmetric cell division. Science 264, 572–575.
2. Wu, L. J., Lewis, P. J., Allmansberger, R., Hauser, P. M., and Errington, J. (1995). A conjugation-like mechanism for prespore chromosome partitioning during sporulation in *Bacillus subtilis*. Genes Devel. 9, 1316–1326.
3. Wu, L. J. and Errington, J. (unpublished data).
4. Sharpe, M. E. and Errington, J. (1996). The *Bacillus subtilis* soj-spoOJ locus is required for a centromere-like function involved in prespore chromosome partitioning. Mol. Microbiol. 21, 501–509.
5. Ogasawara, N. and Yoshikawa, H. (1992). Genes and their organization in the replication origin region of the bacterial chromosome. Mol. Microbiol. 6, 629–634.
6. Mysliwiec, T. H., Errington, J., Vaidya, A. B., and Bramucci, M. G. (1991). The *Bacillus subtilis* spoOJ gene: evidence for involvement in catabolite repression of sporulation. J. Bacteriol. 173, 1911–1919.
7. Williams, D. R. and Thomas, C. M. (1992). Active partitioning of bacterial plasmids. J. Gen. Microbiol. 13 8, 1–16.
8. Ireton, K., Gunther, N. W. IV, and Grossman, A. D. (1994). spoOJ is required for normal chromosome segregation as well as the initiation of sporulation in *Bacillus subtilis*. J. Bacteriol. 176, 5320–5329.
9. Mohl, D. A. & Gober, J. W. (1997) Cell cycle-dependent polar localization of chromosome partitioning proteins in *Caulobacter crescentus*. Cell 88, 675–684.
10. Glaser, P., Sharpe, M. E., Raether, B., Perego, M., Ohlsen, K. & Errington, J. (1997) Dynamic, mitotic-like behaviour of a bacterial protein required for accurate chromosome partitioning. Genes Devel. 11, 1160–1168.
11. Sterlini, J. M. and Mandelstam, J. (1969). Commitment to sporulation in *Bacillus subtilis* and its relationship to the development of actinomycin resistance. Biochem. J. 113, 29–37.
12. Partridge, S. R. and Errington, J. (1993). The importance of morphological events and intercellular interactions in the regulation of prespore-specific gene expression during sporulation in *Bacillus subtilis*. Mol. Microbiol. 8, 945–955.

What is claimed is:

1. A method of determining whether an agent inhibits SpoOJ function in Bacillus species, which method comprises providing a Bacillus strain having a functional SpoOJ gene and having a chromosome with the following modifications;

a) a mutation of a spoIIIE gene which blocks transfer of the prespore chromosome, b) a mutation of soj which prevents loss of SpoOJ function from blocking sporulation, together with c) a first reporter gene having a promoter which is dependent on $\sigma^F$ factor and placed at a location on said chromosome where impaired SpoOJ function leads to increased trapping of said first reporter gene and hence to increased expression thereof in the prespore, and/or d) a second reporter gene having a promoter which is dependent on $\sigma^F$ factor and placed at a location on said chromosome where impaired SpoOJ function leads to reduced trapping of said second reporter gene and hence to reduced expression thereof in the prespore, inducing said Bacillus strain to divide asymmetrically, as during sporulation, in the presence of the agent, and observing expression of the first and/or the second reporter gene.

2. The method as claimed in claim 1, wherein the expression of the first and/or second reporter gene(s) are/is observed by monitoring the levels of their expression products.

3. The method as claimed in claim 2, wherein the first and/or second reporter gene(s) are/is expressed as enzymes whose activities are observed by fluorimetry or spectrophotometry.

4. The method as claimed in claim 1, wherein the Bacillus strain is induced to sporulate and is contacted, just prior to asymmetric cell division, with the agent.

5. The method as claimed in claim 1, which is a screening test for putative antimicrobial agents.

6. The method as claimed in claim 1, wherein the first reporter gene c) and the second reporter gene d) are each fused to a $\sigma^F$-dependent factor gpr promoter.

7. The method as claimed in claim 1, wherein the first reporter gene c) and the second reporter gene d) each express a different detectable enzyme.

* * * * *